United States Patent [19]
Bonissone et al.

[11] Patent Number: 5,942,689
[45] Date of Patent: Aug. 24, 1999

[54] SYSTEM AND METHOD FOR PREDICTING A WEB BREAK IN A PAPER MACHINE

[75] Inventors: Piero Patrone Bonissone, Schenectady; Yu-To Chen; Pratap Shankar Khedkar, both of Niskayuna, all of N.Y.

[73] Assignee: General Electric Company, Schenectady, N.Y.

[21] Appl. No.: 08/943,802

[22] Filed: Oct. 3, 1997

[51] Int. Cl.$^6$ ................................................. G01N 29/10
[52] U.S. Cl. .............................. 73/598; 73/159; 73/865.8
[58] Field of Search ........................... 73/598, 600, 159, 73/865.8

[56] References Cited

U.S. PATENT DOCUMENTS

| | | | |
|---|---|---|---|
| 4,335,316 | 6/1982 | Glanz et al. | 250/572 |
| 5,036,706 | 8/1991 | Gnuechtel et al. | 73/597 |
| 5,130,557 | 7/1992 | Kettl | 250/561 |
| 5,301,866 | 4/1994 | Veh et al. | 226/11 |
| 5,467,194 | 11/1995 | Pellinen et al. | 250/559.29 |
| 5,652,388 | 7/1997 | Callan et al. | 73/628 |

OTHER PUBLICATIONS

"Handbook For Pulp & Paper Technologists" by GA Smook, 1934, pp. 179–243.

"Papermaking and Paperboard Making" By HC Schwalbe, pp. 19–102.

Retention: The Key to Efficient Papermaking by TM Gallagher, etal, 1992 Wet End Operations Short Course, pp. 461–472.

"Fourdrinier Papermaking" by G. Gavelin, Chap 8 & Chap 9, pp. 159–181, (No date).

"1993 Wet End Operations Short Course", Sessions 1–2, 1–3,2–1,6–1,7–2, Ref. No 14 & 15, pp. 23–546.

"Optimization and Simulation of Quality Properties in Paper Machine with Neural Networks" by J. Lampinen, et al, 1994 IEEE, pp. 3812–3815.

"Configurability in a Diagnostic Expert System for Paper Machine Dryer Sections" A by JR Amyot, et al, 8 pages. (No date).

"Paper and Paperboard Manufacturing and Converting Fundamentals" by James E. Kline, pp. 81–126. (No date).

*Primary Examiner*—Max H. Noori
*Attorney, Agent, or Firm*—David C. Goldman; Jill M. Breedlove

[57] ABSTRACT

In this invention there is disclosed a system and method for predicting web breaks in a paper machine. In particular, this invention uses a neural network to predict web break tendencies from sensor measurements taken from the paper machine. Also, an induction tree model is used to isolate the root cause of the predicted web break tendencies.

40 Claims, 7 Drawing Sheets

SYSTEM AND METHOD FOR PREDICTING A WEB BREAK IN A PAPER MACHINE

FIELD OF THE INVENTION

The present invention relates generally to a paper machine and more particularly to a system and method for predicting web break tendencies in the paper machine and isolating machine variables affecting the predicted web break tendencies.

BACKGROUND OF THE INVENTION

A paper machine of the Fourdrinier type typically comprises a wet-end section, a press section, and a dry-end section. At the wet-end section the papermaking fibers are uniformly distributed onto a moving forming wire. The moving wire forms the fibers into a sheet and enables pulp furnish to drain by gravity and dewater by suction. The sheet enters the press section and is conveyed through a series of presses where additional water is removed and the web is consolidated (i.e., the fibers are forced into more intimate contact). At the dry-end section, most of the remaining water in the web is evaporated and fiber bonding develops as the paper contacts a series of steam-heated cylinders. The web is then pressed between metal rolls to reduce thickness and smooth the surface and wound onto a reel.

A problem associated with the Fourdrinier type paper machine is that the paper web is prone to break at both the wet-end section of the machine and at the dry-end section. Web breaks at the wet-end section which typically occur at or near the site of its center roll occur more often than breaks at the dry-end section. Dry-end breaks are relatively better understood, while wet-end breaks are harder to explain in terms of causes and are harder to predict and/or control. Web breaks at the wet-end section can occur as much 15 times in a single day. Typically, for a fully operational paper machine there may be as much as 35 web breaks at the wet-end section of the paper machine in a month. The average production time lost as a result of these web breaks is about 1.6 hours per day. Considering that each paper machine operates continuously 24 hours a day, 365 days a year, the downtime associated with the web breaks translates to about 6.66% of the paper machine's annual production, which results in a significant reduction in revenue to a paper manufacturer. Therefore, there is a need to reduce the amount of web breaks occurring in the wet-end section of a paper machine.

SUMMARY OF THE INVENTION

This invention has developed a system and method for predicting web breaks in either the wet-end section or the dry-end section of the paper machine. In addition, this invention is able to isolate the root cause of any of the predicted web breaks. Thus, in accordance with this invention, there is provided a plurality of sensors for obtaining a plurality of measurements from the paper machine. Each of the plurality of measurements relate to a paper machine variable. A processor processes each of the plurality of measurements into a predetermined break range. A break predictor responsive to the processor, predicts the tendencies of web breaks within the paper machine from the plurality of processed measurements.

DETAILED DESCRIPTION OF THE INVENTION

Figure 1:
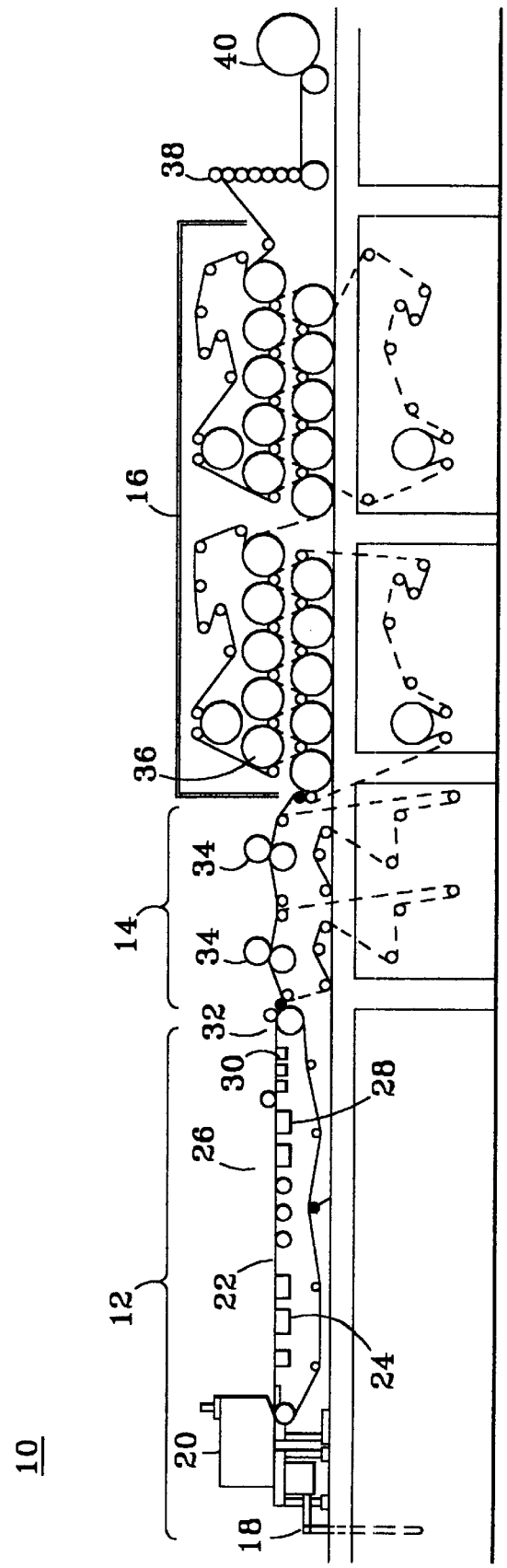
FIG. 1 shows a schematic diagram of a paper machine according to the prior art.

FIG. 1 shows a schematic diagram of a paper machine 10 according to the prior art. The paper machine 10 comprises a wet-end section 12, a press section 14, and a dry-end section 16. At the wet-end section 12, a flowspreader 18 distributes papermaking fibers (i.e., a pulp furnish of fibers and filler slurry) uniformly across the machine from the back to the front. The papermaking fibers travels to a headbox 20 which is a pressurized flowbox. The pulp furnished is jetted from the headbox 20 onto a moving paper surface 22, which is an endless moving wire. The top section of the wire 22, referred to as the forming section, carries the pulp furnish. Underneath the forming section are many stationary drainage elements 24 which assist in drainage. As the wire 22 with pulp furnish travels across a series of hydrofoils or table rolls 26, white water drains from the pulp by gravity and pulsation forces generated by the drainage elements 24. Furnish consistency increases gradually and dewatering becomes more difficult as the wire 22 travels further downstream. Vacuum assisted hydrofoils 28 are used to sustain higher drainage and then highvacuum flat boxes 30 are used to remove as much water as possible. A suction couch roll 32 provides suction forces to improve water removal.

The sheet is then transferred from the wet-end section 12 to the press section 14 where the sheet is conveyed through a series of presses 34 where additional water is removed and the web is consolidated. In particular, the series of presses 34 force the fibers into intimate contact so that there is good fiber-to-fiber bonding. In addition, the presses 34 provide surface smoothness, reduce bulk, and promote higher wet web strength for good runnability in the dry-end section 16. At the dry-end section 16, most of the remaining water in the web is evaporated and fiber bonding develops as the paper contacts a series of steam-heated cylinders 36. The cylinders 36 are referred to as dryer drums or cans. The dryer cans 36 are mounted in two horizontal rows such that the web can be wrapped around one in the top row and then around one in the bottom row. The web travels back and forth between the two rows of dryers until it is dry. After the web has been dried, the web is transferred to a calender section 38 where it is pressed between metal rolls to reduce thickness and smooth the surface. The web is then wound onto a reel 40.

Figure 2:
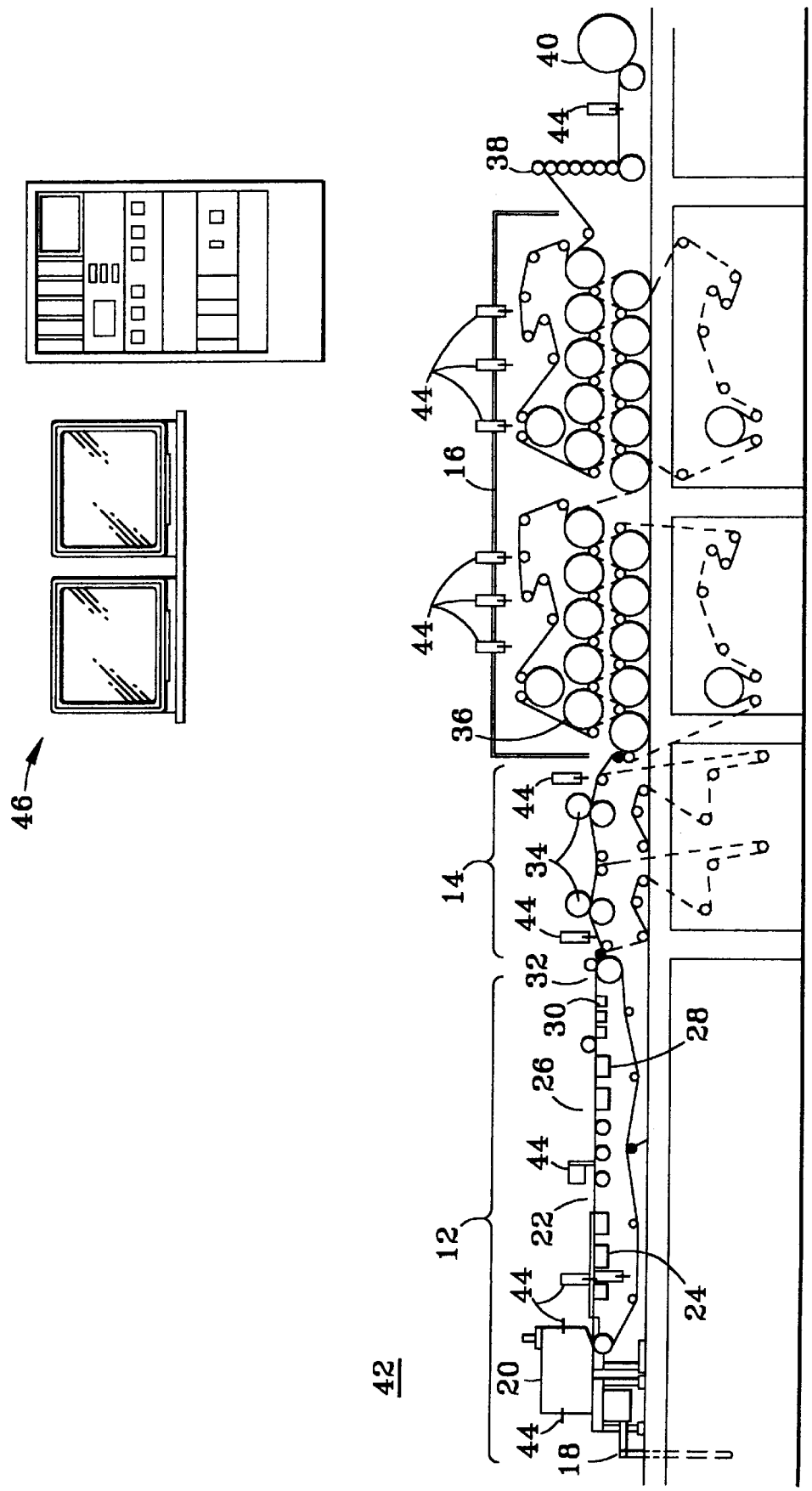
FIG. 2 shows a schematic of a paper machine according to this invention.

As mentioned earlier, the conventional paper machine is plagued with the paper web breaks at both the wet-end section of the machine and at the dry-end section. FIG. 2 shows a schematic of a paper machine 42 that is capable of predicting paper web breaks and isolating the root causes for the breaks. In addition to elements described with respect to FIG. 1, the paper machine 42 comprises a plurality of sensors 44 for obtaining various measurements throughout wet-end section 12, the press section 14, and the dry-end section 16. There are hundreds of different types of sensors (e.g., thermocouples, conductivity sensors, flow rate sensors) located throughout the paper machine 42. For example, there may be as many as 374 sensors located throughout the wet-section of the paper machine 42. For ease of illustration, the sensors 44 are shown in FIG. 2 as substantially the same symbol even though there are many different types of sensors used that are typically designated by different configurations. Each sensor 44 obtains a different measurement that relates to a paper machine variable. Some examples of the type of measurements that may be taken are chemical pulp feed, wire speed, wire pit temperature, wire water pH, and ash content. Note that these measurements are only possible examples of some of the measurements obtained by the sensors 44 and this invention is not limited thereto.

A computer 46, coupled to the paper machine 42 receives each of the measurements obtained from the sensors 44. The computer 46 preprocesses the measurements into a predetermined break range. The preprocessing steps are described below in more detail. After processing, the computer 46 uses a neural network to predict the tendencies of web breaks within the paper machine from the processed measurements. The neural network and the steps performed by the network are also described below in more detail. In addition, the computer 46 uses an induction tree model to generate a set of rules that links paper machine variables measured by the sensors to the predicted web breaks. Thus, the induction tree model can be used as a diagnostic tool to isolate the root cause of the predicted web break. The induction tree model and the rules set derived by the induction tree are described below in more detail.

Figure 3:
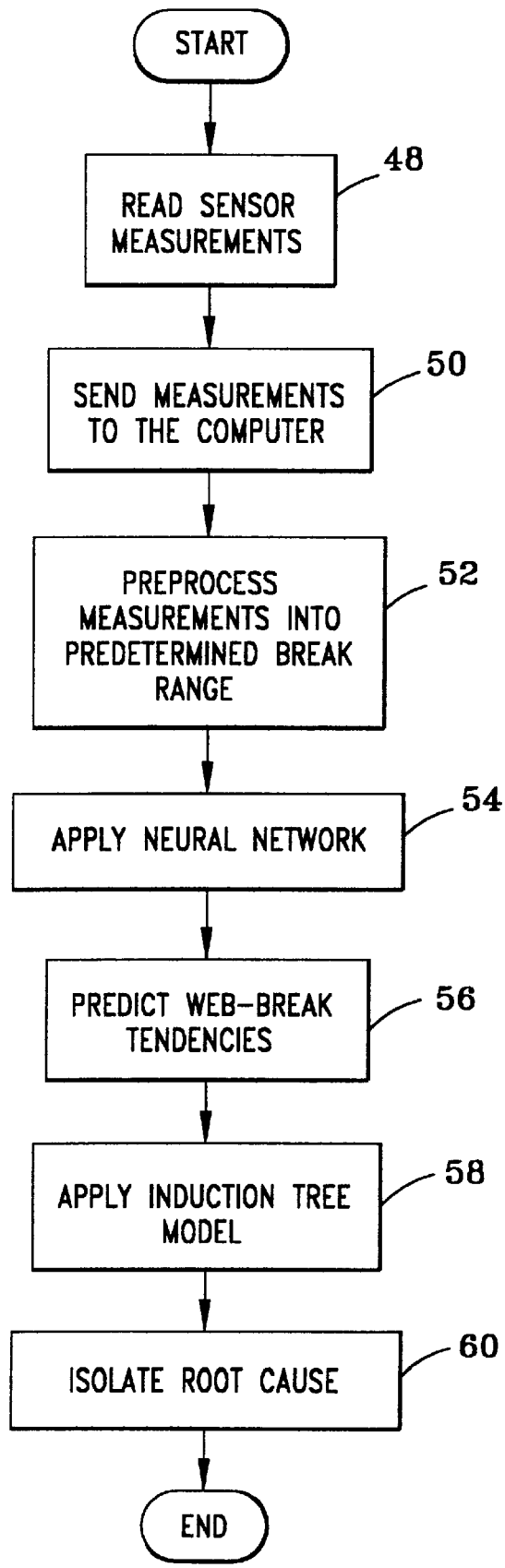
FIG. 3 is a flow chart setting forth the steps used in this invention to predict a web break in a paper machine and isolate the root cause of the break.

FIG. 3 is a flow chart setting forth the steps used in this invention to predict a web break in the wet-end section of the paper machine 42 and isolate the root cause of the break after both the neural network and induction tree model have been sufficiently trained and tested. In FIG. 3, the plurality of sensors 44 located about the paper machine 42 are read at 48. Each of the sensor readings relate to a paper machine variable. As will be explained below, only about 17 input variables are used from the 374 possible sensor readings. Those skilled in the art will realize that more or less input variables may be used in conjunction with this invention. After obtaining the sensor readings, the measurements are sent to the computer 46 at 50. The computer then preprocesses the measurements into a predetermined break range at 52. In particular, the measurements are processed into a range of [0, 1]. After preprocessing, the computer 46 applies the neural network at 54 to the processed measurements. The neural network then predicts the tendencies of any web breaks within the paper machine 42 at 56. Next, the induction tree model is applied at 58 and used to isolate the root cause of the predicted web break tendencies at 60 from its rule set.

Figure 4:
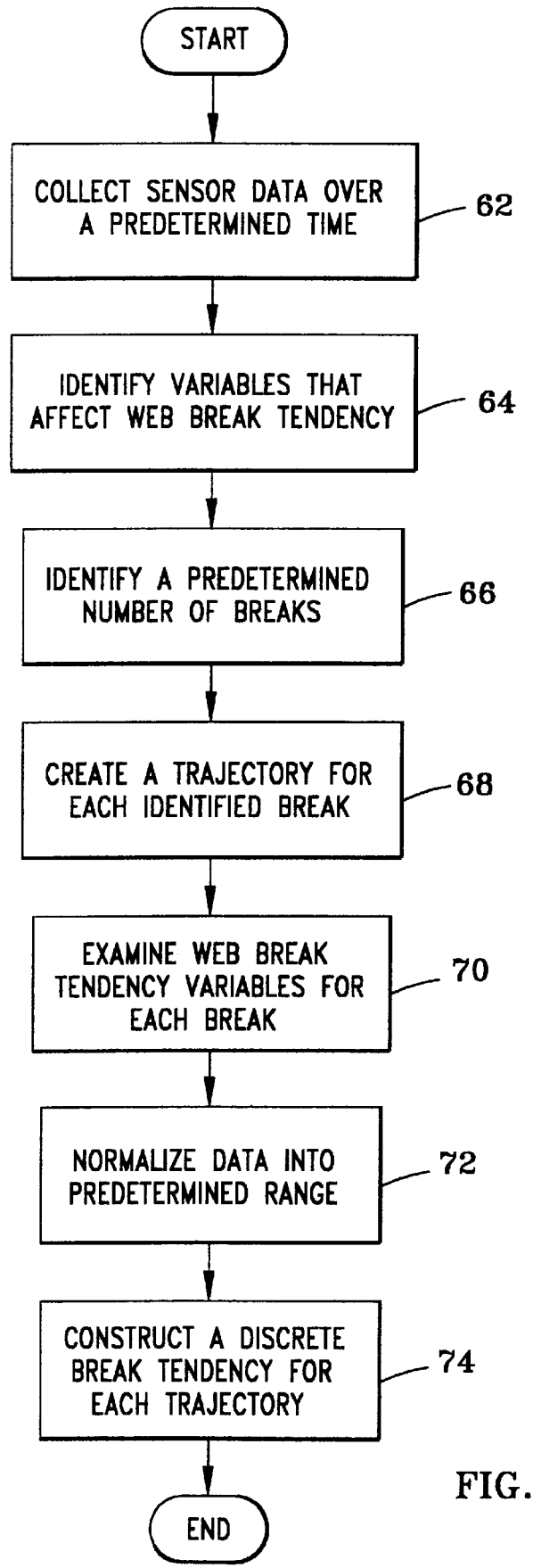
FIG. 4 is a flow chart setting forth the steps used in this invention to acquire historical web break data and preprocess the data.
Figure 6:
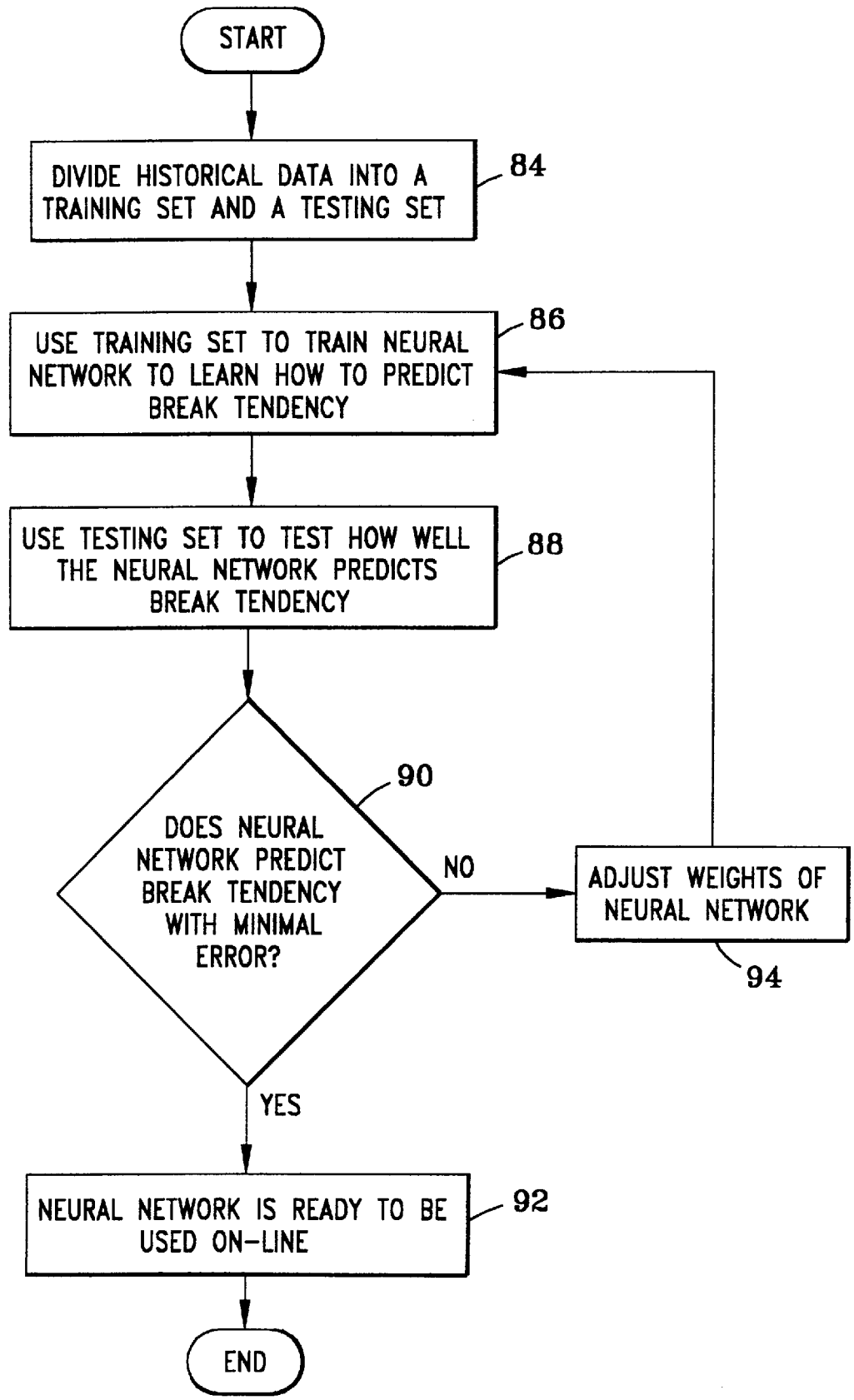
FIG. 6 is a flow chart setting forth the steps used to train and test the neural network in this invention.
Figure 7:
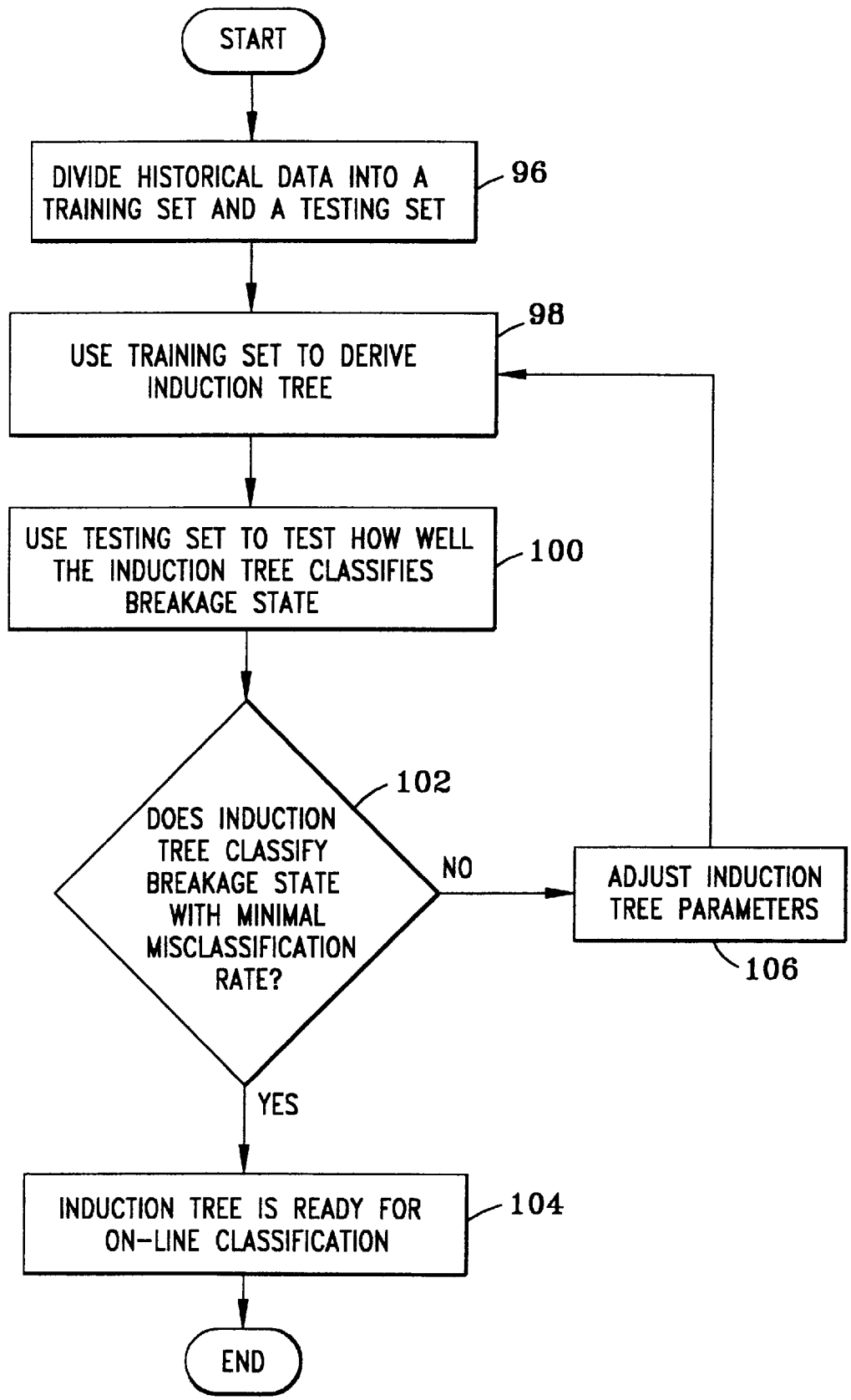
FIG. 7 is a flow chart setting forth the steps used to train and test the induction tree model in this invention.

In order for this invention to be able to predict web break tendencies and to isolate the root cause of the web break tendencies, the computer 46 containing the neural network and the induction tree model have to be trained with historical web break data. A flow chart describing the training steps performed in this invention are set forth in FIGS. 4, 6, and 7. FIG. 4 describes the historical web break data acquisition steps and the preprocessing steps of the data that are used in this invention for training. At 62, sensor data from a paper machine such as the machine described in FIG. 2 is collected over a predetermined time period. In this invention, sensor data from all of the 374 sensors located about the wet-end section of the paper machine were collected over a two to three month period. Note that this time period is illustrative of a preferred time period for collecting a sufficient amount of data and this invention is not limited thereto. Using a sampling time of one minute results in about 1440 samples during a 24 hour period of time and a very large data set over the two to three month period.

After the historical data has been collected, then the data is examined at 64 to identify the paper machine variables that affect the web break tendency. In this invention it has been determined that the paper machine variables that affect the web break tendency the most are paper strength and paper stickiness. Note that these variables and number of measurements are illustrative of only some of the variables and measurements that could be used and this invention is not limited thereto. A list of the sensor readings that relate to the paper strength and paper stickiness are set forth below in Tables 1 and 2.

Measurements Affecting Paper Strength

TMP Feed
Chemcial Pulp Feed
Broke Feed
Chemical Pulp Freeness
Slice Lip Position
Wire Section Speed
Filler To Centrifugal Cleaner Pump
Total Retention
Wire Pit Temperature
Ash Content
K Moisture Table 1

Measurements Affecting Paper Stickiness

Filler To Centrifugal Cleaner Pump
Total Retention
Wire Pit Temperature
Ash Content
K Moisture
Bleached TMP Percentage
Ash Retention
Wire Water pH
Headbox Conductivity
Headbox Temperature
Retention Aid Flow Table 2

Note that there are a total of 22 measurements relating to the paper strength and paper stickiness variables. Five measurements (i.e., Ash Content, K Moisture, Wire Pit Temperature, Total Retention, and Filler To Centrifugal Cleaner Pump) are common to both the paper strength and paper stickiness variables. Thus, the total number of sensor measurements that are related to the web break tendency in this embodiment are 17. Again it is noted that this number is meant to be illustrative and is not meant to limit this invention thereto.

The very large historical data set can now be reduced after the web break variables have been determined. In particular, a predetermined number of web breaks are identified at 66. In this invention, about 40 to 50 web breaks is a sufficient amount. For each web break, a trajectory of data is created over a predetermined window at 68. In this invention, the trajectory of data is created in a 40 minute window ending with the break. In this window the identified variables noted above are examined at 70. This trajectory allows the very large data set to be significantly reduced to a more manageable number. Next, each input variable is normalized linearly to the range of [0, 1] at 74. The equation for normalization is defined as:

$$\text{Normalized Value} = \frac{\text{value} - \text{minimum value}}{\text{maximum value} - \text{minimum value}}, \quad (1)$$

wherein the minimum and maximum values are obtained across one specific field. After the input variables have been normalized, then a discrete break tendency is constructed at 72 for each trajectory of data. In particular, the first ten data points in the trajectory are assigned a value of 0, the next 20 data points are assigned a value of 0.5, and the last ten data points are assigned a value of 1. This labeling scheme represents the degree of break possibility, where 0 represents a low possibility, 0.5 represents a medium possibility, and 1 represents a high possibility.

Figure 5:
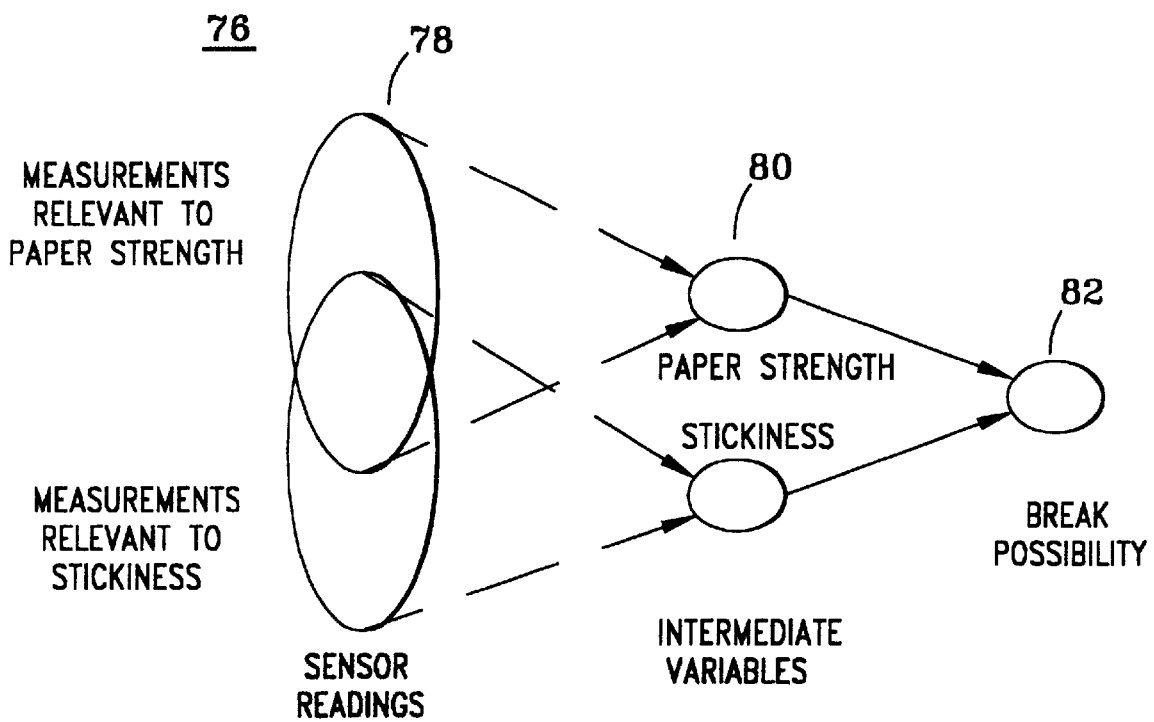
FIG. 5 shows a schematic of a neural network used in accordance with this invention.

After the historical data has been acquired and processed it is then used to train and test the neural network. FIG. 5 shows a schematic of a neural network 76 that is used in this invention. The neural network 76 is preferably a multi-layered feed-forward neural network having an input layer 78, a hidden layer 80, and an output layer 82. In the preferred embodiment, there are 17 input nodes in the input layer, 17 hidden nodes in the hidden layer, and one output node in the output layer. Each of the 17 input nodes are assigned a particular sensor reading taken from the paper machine and are fed forward to each node in the hidden layer. The 17 hidden nodes correspond to intermediate variables that relate to the paper strength and paper stickiness variables and are fed forward to the output node which corresponds to the discrete break tendency described above (i.e., first ten data points are assigned a value of 0, next 20 data points are assigned a value of 0.5, and the last ten data points are assigned a value of 1). The connections between the input nodes, the hidden nodes, and the output node are made via adjustable-weight links. The connection weights are iteratively adjusted using a back propagation algorithm with a set of training data.

In order for the neural network 76 to be used for predicting the web break tendency, it has to be trained and tested with the historical data. A flow chart describing the training and testing steps performed in this invention is set forth in FIG. 6. At 84, the historical data set is divided into two parts, a training set and a testing set. The training set is used to train the neural network 76 to predict the web break tendency and the testing set is used to test the prediction performance of the network when presented with a new data set. If the training is successful, then the neural network is expected to do reasonably well for the data set that it has never seen before. At 86, the training set is used to train the neural network 76 to predict the web break tendency. In this invention, the neural network 76 is trained by using error back-propagation, which is a generalization of the Least Mean Squares (LMS) algorithm. This is essentially a gradient descent method over weight space, which seeks to minimize the mean squared error over the entire training set. Since gradient descent can be very slow, an acceleration technique using fuzzy rules is used to speed up neural network learning.

The basic weight update equation in backpropagation training is as follows:

$$W_{ij}^{s+1}(l) = W_{ij}^s(l) - \eta \frac{\partial E}{\partial W_{ij}^s(l)} + \alpha [W_{ij}^s(l) - W_{ij}^{s-1}(l)], \quad (2)$$

wherein $W_{ij}(l)$ is the weight between the ith neuron at the lth layer and the jth neuron at the (l−1)th layer, E is the sum of squared error between the target and actual output, s is the iteration step, $\eta$ is the learning rate (usually between 0.01 and 1.0), and $\alpha$ is the momentum coefficient (usually 0.9). From the above equation, it is clear that the efficiency of weight updating depends on the selection of the learning rate as well as the momentum coefficient. In general, a large $\eta$ and $\alpha$ result in fast error convergence, but poor accuracy. On the other hand, a small $\eta$ and $\alpha$ lead to better accuracy but slower training. The selections are made ad hoc, i.e., based on empirical results or trial and error. In addition, the choice of an activation function, f(x) influences the learning process. In this invention the activation function is defined as:

$$f(x) = \frac{1}{1 + e^{\frac{1}{2}\beta x}}, \quad (3)$$

wherein $\beta$ is the steepness parameter of the activation function.

The fuzzy accelerator technique that is used in this invention tunes $\eta$, $\alpha$, and $\beta$ simultaneously. Both the total error and total training time are used as fuzzy premise variables for adjusting $\beta$. It is believed that total training time will provide the annealing effect which yields precise convergence. Fuzzy rules for adjusting of $\eta$ and $\alpha$ are listed in below in Table 3, while fuzzy rules for $\beta$ are shown below in Table 4.

TABLE 3

| Change of | Training Error | | |
|---|---|---|---|
| Error | Small | Medium | Big |
| Negative | Very Small Increase | Very Small Increase | Small Increase |
| Zero | No Change | No Change | Small Increase |
| Positive | Small Decrease | Medium Decrease | Large Decrease |

TABLE 4

| | Training Error | | |
|---|---|---|---|
| Training Time | Small | Medium | Big |
| Short | Medium | Small | Small |
| Medium | Large | Medium | Small |
| Long | Large | Large | Medium |

In Table 3 the universe of discourse of the total training error is partitioned into Small, Medium, and Big, while the universe of discourse of the change of error between two consecutive iterations is partitioned into Negative, Zero, and Positive. There are nine fuzzy rules for adjustment of both the learning rate and the momentum coefficient. This enables the training time to be reduced significantly even with such simple fuzzy rules. In Table 4, the partitioning of total training error is the same as in Table 3, while the universe of discourse of total training time is partitioned into Short, Medium, and Long. Again, there are nine rules for adjustment of the steepness parameter of the activation function. For instance, the fuzzy rule in row 3 column can be interpreted as:

IF error is Small AND time for training is long
THEN steepness parameter should be Large Performance indices can be used to measure how well the neural network 76 was trained. Two performance indices that may be used are the mean squared error (MSE) and the R squares ($R^2$). The mean squared error is defined as:

$$MSE = \frac{1}{p} \times \sum_{i=1}^{p} (T_i - O_i)^2, \quad (4)$$

wherein p is the number of patterns in training and testing and $T_i$ and $O_i$ are the ith targeted output and calculated output, respectively. The smaller the MSE, the closer the calculated output is to the targeted output. The $R^2$ performance indices is defined as:

$$R^2 = 1.0 - \left( \frac{\sum_{i=1}^{p} (T_i - O_i)^2}{\sum_{i=1}^{p} (T_i - \overline{T})^2} \right), \quad (5)$$

wherein $\overline{T}$ is the mean of targeted outputs. The $R^2$ removes the effects of target variance and yields an error value usually between 0 and 1. The closer the $R^2$ value is towards 1, the better the performance. In particular, $R^2$ is particular useful for back-propagation type neural networks, since a back-propagation network learns relatively easily the pattern represented by the average target values of the output nodes. This is a sort of a "worst case" scenario in which the neural network is "guessing" the correct output to be the average target value, and results in a value of $R^2$ of 0. As the patterns are learned, the value of $R^2$ moves toward 1.

Referring back to FIG. 6, after the neural network 76 is trained, the testing set of data is then used to test how well the trained neural network predicts the break tendency at 88. The testing is measured by using the aforementioned performance indices. If the trained neural network does predict the break tendency with minimal error (e.g. $10^{-3}$) at 90, then the network is ready to be used on-line at 92 to predict the break tendency. However, if the trained neural network is unable to predict the break tendency with minimal error at 90, then the weights are adjusted at 94 and steps 86–90 are repeated until the error becomes small enough.

After the neural network 76 has been trained to predict the break tendency, the induction tree model is now trained to derive a set of rules that can explain any predicted break tendencies. Decision trees are well known and have been used extensively for classification and root cause analysis. In this invention, the well known C4.5 algorithm is used to generate a classification tree from data. The C4.5 algorithm is a well-tested approach in machine learning applications, that structures the tree so as to maximize the information gained by the split at each node of the tree. In this invention, the C4.5 is employed to produce decision trees to classify breakage conditions (i.e., low, medium, high) as output for a given data set. In particular, the C4.5 algorithm uses the data acquired in FIG. 4 as input and produces a classification tree as an output. From the classification tree, a set of rules that explains any predicted break tendencies can be derived.

In order for the induction tree to be used for deriving a set of rules that explains break tendencies, it has to be trained and tested with the historical data. A flow chart describing the training and testing steps of the induction tree is set forth in FIG. 7. At 96, the historical data set is divided into two parts, a training set and a testing set. The training set is used derive an induction tree and the testing set is used to test the classification performance of the induction tree when presented with a new data set. If the training is successful, then the induction tree is expected to do reasonably well for the data set that it has never seen before. At 98, the training set is used in conjunction with the C4.5 algorithm to derive an induction tree and a set of classification rules. After the induction tree has been derived, the testing set of data is then used to test how well the induction tree classifies the breakage state at 100. If the induction tree does classify the breakage state with a minimal misclassification rate at 102, then the induction tree is ready to be used for on-line classification at 104. However, if the induction tree is unable to classify the breakage state with a minimal error at 102, then the induction tree parameters (i.e., splitting criteria, stopping criteria, node selection, etc.) are adjusted at 106 and steps 98–102 are repeated until there is a minimal misclassification rate.

An example of some of the rules that are derived from the induction tree are listed below. This list is illustrative of some of the possible rules that may be derived in this invention and is not exhaustive of all of the possible set of rules that can be generated.

Rule 25:
 Chemical_pulp_feed<=0.642256
 Chemical_pulp_freeness>0.314925
 Slice_lip_position<=0.687364
 Headbox_conductivity>0.328703
 Headbox_temperature>0.398742
 Headbox_temperature<=0.634154
 Retention_aid_flow>0.259781
 Retention_aid_flow<=0.342345→class high Rule 25 states that there is a high possibility of break if the chemical pulp feed, chemical pulp freeness, slice lip position, headbox conductivity, headbox temperature, and retention aid flow values measured from the sensor satisfy the above equations.

Rule 32:
 Chemical_pulp_freeness<=0.526866
 Slice_lip_position<=0.729194
 Ash_retention>0.560629
 Wire_water_pH>0.10404
 Headbox_temperature>0.634154
 Retention_aid_flow>0.316287→class low Rule 32 is an example of a rule that indicates that there is a low possibility of a break. This rule states that there is a low possibility of break if the chemical pulp freeness, slice lip position, ash retention, wire water pH, headbox temperature, and retention aid flow values measured from the sensor satisfy the above equations.

Rule 4:
 Broke_feed<=0.37506
 Slice lip_position<=0.549291
 Retention_aid_flow<=0.218194→class medium Rule 4 is an example of a rule that indicates that there is a medium possibility of a break. As mentioned earlier, these rules can be used to isolate the root cause of any web break tendencies predicted by the neural network. In particular, if the neural network predicts that there is a tendency for web break in the paper machine, then the induction tree using its rule set may determine that the root cause of this predicted break may be due to certain sensor measurements not being within a certain range.

Although this invention has been described with reference to predicting web breaks and isolating the root cause of the breaks in the wet-end section of the paper machine, this invention is not limited thereto. In particular, this invention can be used to predict web breaks and isolate the root cause in other sections of the paper machine such as the dry-end section and the press section.

It is therefore apparent that there has been provided in accordance with the present invention, a system and method for predicting a web break in a paper machine that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

We claim:

1. A system for predicting a web break in a paper machine, comprising:
   a plurality of sensors for obtaining a plurality of measurements from the paper machine, each of the plurality of measurements relating to a paper machine variable;
   a processor for processing each of the plurality of measurements into a predetermined break range; and
   a break predictor responsive to the processor for predicting tendencies of web breaks within the paper machine from the plurality of processed measurements.

2. The system according to claim 1, wherein the break predictor comprises a neural network.

3. The system according to claim 1, further comprising a fault isolator responsive to the break predictor for determining the paper machine variables affecting the predicted web break tendencies.

4. The system according to claim 3, wherein the fault isolator comprises an induction tree model having a set of rules linking paper machine variables to the predicted web breaks.

5. A method for predicting a web break in a paper machine, comprising the steps of:
   obtaining a plurality of measurements from the paper machine, each of the plurality of measurements relating to a paper machine variable;
   processing each of the plurality of measurements into a predetermined break range; and
   predicting tendencies of web breaks within the paper machine from the plurality of processed measurements.

6. The method according to claim 5, wherein the step of predicting tendencies of web breaks comprises using a neural network.

7. The method according to claim 5, further comprising the step of isolating the paper machine variables affecting the predicted web break tendencies.

8. The method according to claim 7, wherein the step of isolating the paper machine variables affecting the predicted web break tendencies comprises using an induction tree model having a set of rules linking paper machine variables to the predicted web breaks.

9. The system according to claim 1, wherein the predetermined break range comprises the range of [0,1].

10. The system according to claim 2, wherein the neural network is trained with historical web break data.

11. The system according to claim 3, wherein the fault isolator isolates the paper machine variables that are root causes for the predicted web break tendencies.

12. The system according to claim 4, wherein the induction tree model is trained with historical web break data.

13. A system for predicting a web break in a wet-end section of a paper machine, comprising:
   a plurality of sensors for obtaining a plurality of measurements from the wet-end section of the paper machine, each of the plurality of measurements relating to a paper machine variable;
   a processor for processing each of the plurality of measurements into a predetermined break range; and
   a break predictor responsive to the processor for predicting tendencies of web breaks within the wet-end section of the paper machine from the plurality of processed measurements.

14. The system according to claim 13, wherein the predetermined break range comprises the range of [0,1].

15. The system according to claim 13, wherein the break predictor comprises a neural network.

16. The system according to claim 15, wherein the neural network is trained with historical web break data.

17. The system according to claim 13, further comprising a fault isolator responsive to the break predictor for determining the paper machine variables affecting the predicted web break tendencies.

18. The system according to claim 17, wherein the fault isolator isolates the paper machine variables that are root causes for the predicted web break tendencies.

19. The system according to claim 17, wherein the fault isolator comprises an induction tree model having a set of rules linking paper machine variables to the predicted web breaks.

20. The system according to claim 19, wherein the induction tree model is trained with historical web break data.

21. The method according to claim 5, wherein the predetermined break range comprises the rang e of 0,1.

22. The method according to claim 6, further comprising training the neural network with historical web break data to learn how to predict web break tendencies.

23. The method according to claim 22, further comprising testing the trained neural network with the historical break data to test how well the neural network predicts web break tendencies.

24. The method according to claim 22, where in the training comprises preprocessing the historical web break data.

25. The method according to claim 24, where in the preprocessing comprises:
   identifying the paper machine variables that affect historical web break tendency;
   identifying a p redetermined number of historical web breaks;
   creating a trajectory for each identified historical web break;
   examining the paper machine variables in each trajectory; and
   constructing a discrete web break tendency for each trajectory.

26. The method according to claim 7, wherein the step of isolating further comprises isolating the paper machine variables that are root causes for the predicted web break tendencies.

27. The method according to claim 8, further comprising training the induction tree model with historical web break data to derive the set of rules explaining the predicted web break tendencies.

28. The method according to claim 27, further comprising testing the trained induction tree model with the historical break data to test how well the set of rules explains the predicted web break tendencies.

29. A method for predicting a web break in a wet-end section of a paper machine, comprising:

obtaining a plurality of measurements from the wet-end section of the paper machine, each of the plurality of measurements relating to a paper machine variable;

processing each of the plurality of measurements into a predetermined break range; and predicting tendencies of web breaks within the wet-end section of the paper machine from the plurality of processed measurements.

30. The method according to claim 29, wherein the predetermined break range comprises the range of [0,1].

31. The method according to claim 30, wherein the predicting tendencies of web breaks comprises using a neural network.

32. The method according to claim 31, further comprising training the neural network with historical web break data to learn how to predict web break tendencies.

33. The method according to claim 32, further comprising testing the trained neural network with the historical break data to test how well the neural network predicts web break tendencies.

34. The method according to claim 32, wherein the training comprises preprocessing the historical web break data.

35. The method according to claim 34, wherein the preprocessing comprises:

identifying the paper machine variables that affect historical web break tendency;

identifying a predetermined number of historical web breaks;

creating a trajectory for each identified historical web break;

examining the paper machine variables in each trajectory; and constructing a discrete web break tendency for each trajectory.

36. The method according to claim 29, further comprising isolating the paper machine variables affecting the predicted web break tendencies.

37. The method according to claim 36, wherein the isolating further comprises isolating the paper machine variables that are root causes for the predicted web break tendencies.

38. The method according to claim 36, wherein the isolating the paper machine variables affecting the predicted web break tendencies comprises using an induction tree model having a set of rules linking paper machine variables to the predicted web breaks.

39. The method according to claim 38, further comprising training the induction tree model with historical web break data to derive the set of rules explaining the predicted web break tendencies.

40. The method according to claim 39, further comprising testing the trained induction tree model with the historical break data to test how well the set of rules explains the predicted web break tendencies.

* * * * *